(12) United States Patent
Nabeshima et al.

(10) Patent No.: US 7,576,852 B2
(45) Date of Patent: Aug. 18, 2009

(54) SEMICONDUCTOR WAFER INSPECTION DEVICE AND METHOD

(75) Inventors: Fumi Nabeshima, Hiratsuka (JP); Kazuya Togashi, Hiratsuka (JP); Hiroshi Jiken, Hiratsuka (JP); Yoshinori Suenaga, Hiratsuka (JP)

(73) Assignee: Sumco Tech XIV Corporation, Nagasaki (JP)

( * ) Notice: Subject to any disclaimer, the term of this patent is extended or adjusted under 35 U.S.C. 154(b) by 490 days.

(21) Appl. No.: 10/598,933

(22) Filed: Sep. 14, 2006

(65) Prior Publication Data

US 2009/0040512 A1      Feb. 12, 2009

Related U.S. Application Data

(63) Continuation of application No. PCT/JP2005/007120, filed on Apr. 13, 2005.

(30) Foreign Application Priority Data

Apr. 13, 2004   (JP)   ............................. 2004-117910

(51) Int. Cl.
    *G01N 21/00*   (2006.01)
(52) U.S. Cl. ................................. 356/239.7; 356/237.2
(58) Field of Classification Search .............. 356/239.7, 356/237.2
    See application file for complete search history.

(56) References Cited

U.S. PATENT DOCUMENTS

| 6,271,916 | B1 * | 8/2001 | Marxer et al. ............ 356/237.3 |
| 6,515,742 | B1 * | 2/2003 | Ruprecht ................. 356/237.4 |
| 2002/0036771 | A1 | 3/2002 | Sato et al. | |

FOREIGN PATENT DOCUMENTS

| JP | H11-126736 A1 | 5/1999 |
| JP | 2001-176943 A1 | 6/2001 |
| JP | 2002-098645 A1 | 4/2002 |
| WO | WO-01/27600 A1 | 4/2001 |

* cited by examiner

*Primary Examiner*—Roy Punnoose
(74) *Attorney, Agent, or Firm*—Orion Consulting, Ltd.; Joseph Farrar (57) ABSTRACT

The surface of an epitaxial wafer is inspected using an optical scattering method. The intensities of light scattered with a narrow scattering angle and light scattered with a wide scattering angle reflected from laser light scatterers (LLS) on the wafer surface are detected. If the intensifies of narrowly and widely scattered lights are within a prescribed sizing range, it is judged whether the laser light scatterer is a particle or killer defect by deciding into which zone (410, 414, 418, 439) within the sizing range the PLS size based on the narrowly scattered light intensity and the PLS size based, on the widely scattered light intensity fall. If the intensity of the narrowly or widely scattered light exceeds the sizing range (417, 420, 421, 423, 424, 425), or if a plenty of laser light scatterers are continuous or concentrated (422), the laser light scatterers are judged to be killer defects.

6 Claims, 6 Drawing Sheets

FIG. 3D

SEMICONDUCTOR WAFER INSPECTION DEVICE AND METHOD

CROSS REFERENCE TO RELATED APPLICATIONS

The present application is a continuation of PCT/JP 50/07120, filed on Apr. 13, 2005, and is related to and claims priority from Japanese patent application no. 2005-152672, filed on Apr. 13 2004. The content of both of the aforementioned applications are incorporated herein by reference.

TECHNICAL FIELD

The present invention relates to technology for inspecting the surface quality of a semiconductor wafer, suitable, in particular, to the detection of surface defects of an epitaxial wafer.

BACKGROUND ART

In general, semiconductor wafer defects (structural or chemical abnormalities that impair the ideal crystal structure of the surface layer of the semiconductor wafer) are classified in terms of the effect that they have on a semiconductor device that is formed on the wafer into slight defects, which are allowable, and fatal defects. Fatal defects are called "killer defects" and result in a lowering of the yield of semiconductor devices. In particular in the case of epitaxial wafers, the main defects are stacking faults (SF) of the epitaxial layer; usually, these appear as protuberances or concavities of the surface of the semiconductor wafer. Most killer defects are part of such an SF. Killer defects are caused for example by the height being such as to generate a defocusing fault in the process of manufacturing a device, or by a defect termed a large area defect (LAD), having a wide area, that affects several devices. For convenience, defects including surface defects of epitaxial wafers will herein be referred to as ELDs (EP layer defects). Techniques for detecting "killer defects" on the surface of semiconductor wafers are extremely important in semiconductor manufacture.

An abnormality inspection device employing an optical scattering method is widely employed for surface inspection of semiconductor wafers. Using such an abnormality inspection device, the surface of a semiconductor wafer is scanned with a laser beam of minute size and scattered light from laser light scatterers (defects or particles) on the surface of the semiconductor wafer is detected; the size (value corresponding to the size of standard particles (PLS; polystyrene latex)) of laser light scatterers present on the wafer surface is measured from the intensity of this scattered light. Whereas it is impossible to permanently remove defects from semiconductor wafers, particles can be removed by subsequent processing and are not therefore fatal as regards the semiconductor device. Consequently, in surface inspection using an optical scattering method, it is important to be able to distinguish whether the individual laser light scatterers that are detected are defects or particles.

Laid-open Japanese Patent Application No. 2001-176943 discloses a method for detecting stacking faults of epitaxial wafers using an optical scattering method. In this method, using an abnormality detection device employing an optical scattering method (for example a Surfscan 6200 (Trade Mark) manufactured by KLA-Tencor Ltd), the size of laser light scatterers present on the surface of an epitaxial wafer is measured and these laser light scatterers are classified into bodies whose size is no more than 1.6 μm and bodies that exceed this value; laser light scatterers exceeding 1.6 μm are identified as being stacking faults, while laser light scatterers of no more than 1.6 μm are identified as pits other than stacking faults.

DISCLOSURE OF THE INVENTION

The invention disclosed in Laid-open Japanese Patent Application No. 2001-176943 is subject to the following problems.

First of all, defects exist at the wafer surface in a large variety of forms: this makes it difficult to classify such defects in terms of the intensity of the scattered light from a single laser beam with a high degree of certainty. It is even difficult to distinguish between defects and particles. The most that can be achieved with this method is to classify defects into two types, with a threshold value of 1.6 μm. Also, performance of selective etching as pretreatment greatly lowers the throughput of defect inspection, so this method is unsuitable for mass-production and the surface quality of the wafers is impaired by selective etching, to the extent that it may no longer be possible for such wafers to be shipped as products. Further, Laid-open Japanese Patent Application No. 2001-176943 does not discuss classifying laser light scatterers at the wafer surface into killer defects and defects which are not killer defects.

An object of the present invention is therefore to improve the accuracy of surface inspection of semiconductor wafers and in particular epitaxial wafers using an optical scattering method.

A further object is to improve the accuracy of identification of defects and particles in surface inspection of semiconductor wafers and in particular epitaxial wafers using an optical scattering method.

Yet another object is to improve the accuracy of identification of killer defects and defects which are not killer defects in surface inspection of semiconductor wafers and in particular epitaxial, wafers using an optical scattering method.

Also, yet another object is to provide an inspection device or method of inspection that is more suited to mass production.

A semiconductor wafer inspection device according to one aspect of the present invention comprises: an optical illumination device that directs a light spot onto an inspection point on a surface of the semiconductor wafer; a first optical sensor that, of scattered light from said inspection point, receives narrowly scattered light scattered with a scattering angle that is narrower than a prescribed angle and detects intensity of said narrowly scattered light; a second optical sensor that, of scattered light from said inspection point, receives widely scattered light scattered with a scattering angle that is wider than a prescribed angle and detects intensity of said widely scattered light; and a signal processing circuit that identifies the type of laser light scatterer (LLS) present at said inspection point. Said signal processing circuit comprises: first calculation means that, if the intensity of said narrowly scattered light is within a prescribed sizing range, calculates a first PLS-based size from the intensity of said narrowly scattered light; second calculation means that, if the intensity of said widely scattered light is within said sizing range, calculates a second PLS-based size from the intensity of said widely scattered light; and identification means that, if the intensities of said narrowly scattered, light and said widely scattered light are both within said sizing range, identifies the type of said laser light scatterer in accordance with both the first PLS-based size and said second PLS-based size.

In a suitable embodiment, said identification means identifies a laser light scatterer present at said inspection point as being a particle, in a prescribed particle zone in which said first PLS-based size in said sizing range is either substantially equal to said second PLS-based size or is larger than said second PLS-based size, by a degree not more than a prescribed degree.

In a suitable embodiment, said identification means identifies a laser light scatterer present at said inspection point as being a defect, in a prescribed defect zone in which said first PLS-based size in said sizing range is larger than said second PLS-based size, by a degree not less than said prescribed degree. In this case, said identification means identifies whether said defect is assumed to be a killer defect or not, in accordance with whether the first PLS-based size is larger or smaller than a prescribed size, in said defect zone.

In a suitable embodiment, said identification means identifies a laser light scatterer present at said inspection point as being a defect that is assumed to be a killer defect if the intensity of said, narrowly scattered light or said widely scattered light exceeds said sizing range.

A method of inspection of semiconductor wafers according to another aspect of the present invention comprises: a step of directing a light spot onto an inspection point on the surface of the send conductor wafer; a step of detecting the intensity, of the scattered light from said inspection point, of narrowly scattered light scattered with a scattering angle that is narrower than a prescribed angle; a step of detecting the intensity, of the scattered light from said inspection point, of widely scattered light scattered with a scattering angle that is wider than the prescribed angle; a step of, if the intensity of said narrowly scattered light is within a prescribed sizing range, calculating a first PLS-based size from the intensity of said narrowly scattered light; a step of, if the intensity of said widely scattered light is within said sizing range, calculating a second PLS-based size from the intensity of said widely scattered light; and a step of, if the intensities of said narrowly scattered light and said widely scattered light are both within said sizing range, identifying the type of laser light scatterer present at said inspection point in accordance with the magnitude relationship of said, first PLS-based size and said second PLS-based size.

According to the present invention, the accuracy of surface inspection of semiconductor wafers using an optical scattering method can be improved.

DESCRIPTION OF THE PREFERRED EMBODIMENT

Figures 1A, 1B:
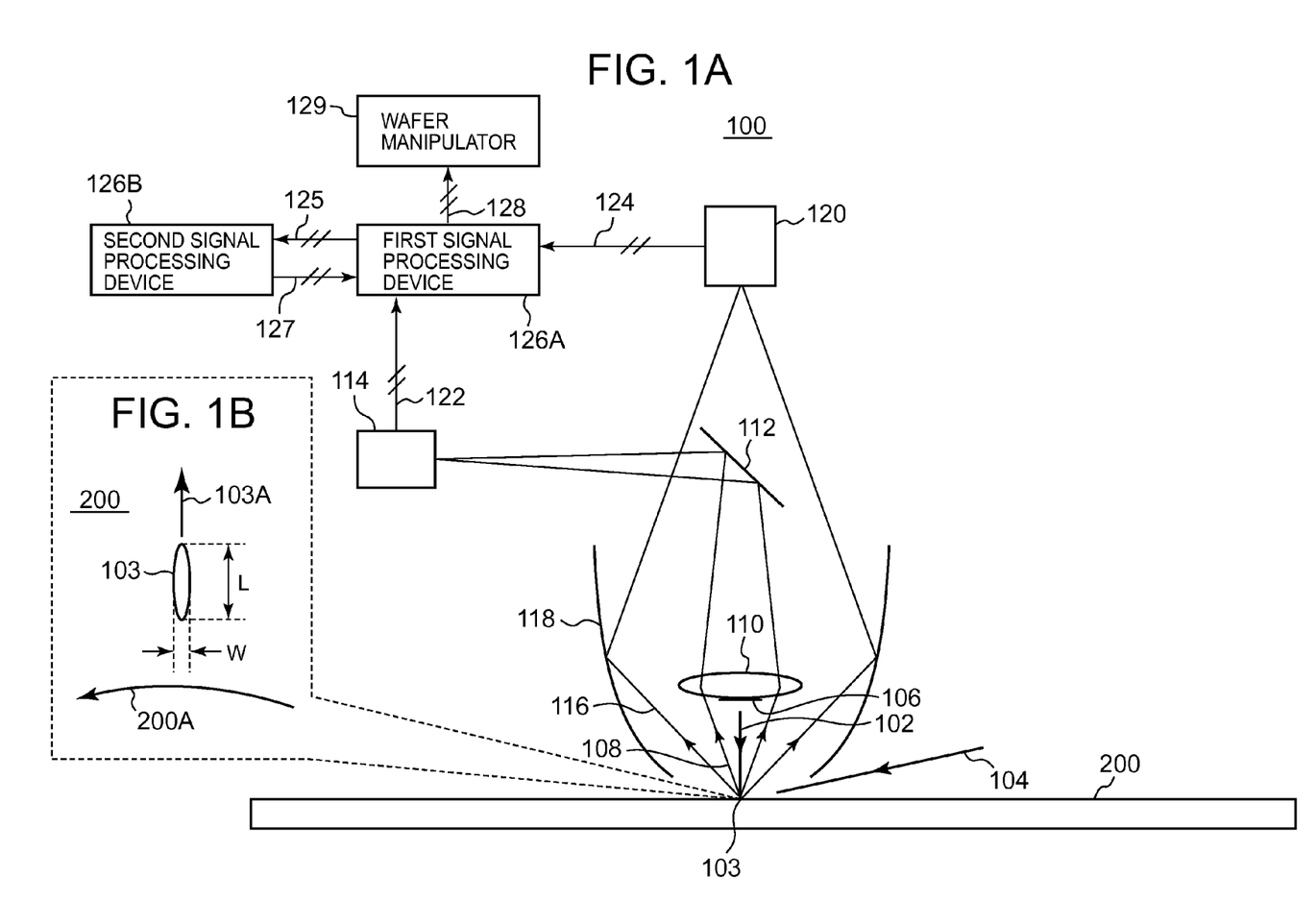
FIG. 1A is a cross-sectional view showing the construction of a semiconductor wafer inspection device according to an embodiment of the present invention.
FIG. 1B is a plan view showing how scanning of a semiconductor wafer surface is conducted using a light spot.

FIG. 1A is a cross-sectional side view showing the construction of a semiconductor wafer inspection device according to an embodiment of the present invention. FIG. 1B, shown in the dotted line balloon block, is a plan view showing how scanning is performed of the semiconductor wafer surface using a light spot.

As shown in FIG. 1A, this inspection device 100 is capable of selectively directing two laser beams 102, 104 onto a point (inspection point) on the surface of a semiconductor wafer 200. One of the laser beams 102 is directed perpendicularly onto the surface of the semiconductor wafer 200 while the other laser beam 102 is directed onto the surface of the semiconductor wafer 200 at an inclined angle. In this embodiment, only the perpendicularly directed laser beam 102 is employed and the laser beam 104 that is directed in inclined fashion is not employed. The inspection point on the surface of the semiconductor wafer 200 is illuminated by a minute laser-spot 103 that is formed by the perpendicularly directed laser beam 102. As shown in FIG. 1B, this laser spot 103 has an elongate elliptical shape; the major diameter and minor diameter thereof face directions that are respectively parallel with the radius and circumferential line of the semiconductor wafer 200. The size of the laser-spot 103 is for example about 50 to 350 μm in the case of the major diameter dimension L and about 20 μm in the case of the minor diameter dimension W. In the Inspection device 100, the semiconductor wafer 200 is rotated about the central point as shown by the arrow 200A of FIG. 1B and, simultaneously, the laser spot 103 is moved along the radius of the semiconductor wafer 200 as shown by the arrow 103A; in this way, the entire region of the surface of the semiconductor wafer 200 is scanned in spiral fashion by the laser spot 103. The interval between the spiral scanning lines (interval of the Nth scanning line and N+1 th scanning line in the radial direction; is about 20 to 180 μm i.e. about half of the major diameter dimension L of the laser spot 103. Consequently, the positional resolution of the inspection result obtained by this scanning is about 20 to 180 μm.

At the inspection point (location where the light spot 103 is incident) on the semiconductor wafer 200, the perpendicularly incident laser beam 102 is reflected in a direction depending on the surface condition at this inspection point. For example, if no defect or particle is present at the inspection point, the surface shape at the inspection point is completely flat, so the perpendicularly incident laser beam 102 is reflected, perpendicularly. On the other hand, if a defect or particle is present at the inspection point, since a protuberance or concavity is present in the surface shape, the reflected light from the perpendicularly incident laser beam 102 forms scattered light 108, 116 in various directions. The perpendicularly reflected beam from the inspection point is absorbed by the mask 106 and is not employed in inspection. On the other hand, part of the scattered reflected light from the inspection point is detected by the optical sensor 114, depending on the scattering angle (reflected angle) thereof, while another part thereof is detected by another optical sensor 120. Specifically, the reflected light 108 that is scattered in a narrow angle range of scattered angle no more than a prescribed value (hereinbelow referred to as "narrowly scattered light") passes through a convex lens 110 and reflecting mirror 112 and is detected by a first optical sensor 114. Also, the reflected light 116 that is scattered in a wide-angle range of scattered angle larger than the prescribed angle (hereinbelow referred to as "widely scattered light") passes through a solid concave reflecting mirror 118 and is detected by a second sensor 120. The first optical sensor 114 generates an electrical signal 122 (for example, a voltage signal) (hereinbelow referred to as the "narrowly scattered, light intensity signal") having a level responsive to the intensity of the narrowly scattered light 108 and this is output to the first signal processing device 126A. The second optical sensor 120 generates an electrical signal (for example, a voltage signal) (hereinbelow referred to as "widely scattered light intensity signal") 124 having a level responsive to the intensity of the widely scattered light 116 and this is output to the first signal processing device 126A. For example photomultiplier tubes may be employed for the optical sensors 114, 120.

A first and second mutually connected signal processing device 126A and 126B are provided. The combination of first and second signal processing devices 126A and 126B, by performing analysis by a method described in detail below, of the input narrowly scattered light intensity signal 122 and widely scattered light intensity signal 124, detects laser light scatterers (hereinbelow referred to as LLS) (these typically correspond to "surface abnormalities" such as for example protuberances or concavities of the wafer surface, in other words, defects or particles) on the surface of the semiconductor wafer 200, identifies the detected LLS as a particle, a severe defect having a high probability of being a killer defect, or a slight defect having a low probability of being a killer defect, and outputs the results of this identification. The first signal processing device 126A, using in particular the narrowly scattered light intensity signal 122 and widely scattered light intensity signal 124, detects laser light scatterers (hereinbelow referred to as LLS) on the surface of the semiconductor wafer 200, and calculates the size and positional co-ordinates thereof. The second signal processing device 126B receives data 125 indicating the size and positional co-ordinates of the LLS from in particular the first signal processing device 126A and identifies whether this LLS is a particle, severe defect or slight defect, and, in accordance with the results of this identification, determines the detection result, i.e. whether the semiconductor wafer 200 is a good product or not, and outputs this determination result and inspection result. Of the output data from the second signal processing device 126B, data 127 indicating at least the above inspection result is input to the first signal processing device 126A. The first signal processing device 126A outputs a sorting instruction signal 128 corresponding to this inspection result to a wafer manipulator 129. The wafer manipulator 129 sorts the semiconductor wafers 200 whose inspection has been completed into good products and defective products in accordance with the sorting instruction signal 128. The first and second signal processing devices 126A and 126B can respectively be implemented by for example a programmed computer, dedicated hardware circuit or a combination of these.

For the portion of this inspection device 100 excluding the second signal processing device 126B, for example an SP1 (Trade Mark; manufactured by KLA-Tencor Ltd may be used. This inspection device 100 can therefore be realized by adding the signal analysis function of the second signal processing device 126B to this SP1.

Figure 2:
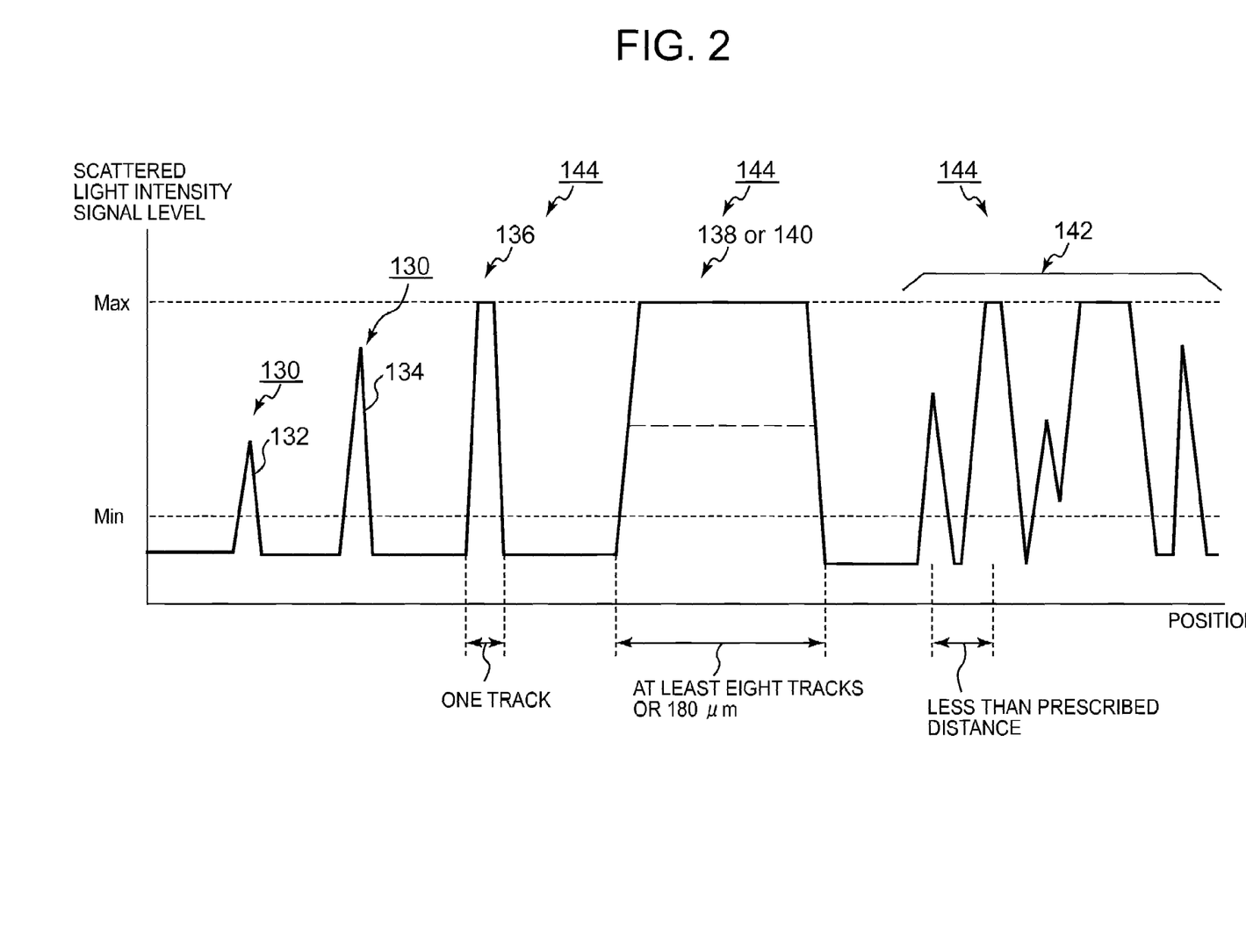
FIG. 2 is a waveform diagram showing a plurality of types of light intensity signal 122, 124 output from optical sensors 114, 120.

FIG. 2 is a waveform diagram showing different types of scattered light intensity signals 122, 124 that may be analysed by the signal processing devices 126A and 126B. The type shown in FIG. 2 may be applied to both the widely scattered light intensify signal 122 and narrowly scattered light intensity signal 124.

As shown in FIG. 2, the scattered light intensity signals 122, 124 that may be analyzed by the signal processing device 126 may be broadly classified into five types, namely, 130, 136, 138, 140 and 142, depending on the signal level (for example voltage level). The first type 130 is a type in which the peak value of the signal level is within the range of at least a prescribed lower limiting level Min but less than a prescribed maximum level Max. This prescribed lower limiting level Min is the minimum signal level at which it can be recognised that an LLS has been detected (i.e. level at which it cannot be recognized that an LLS exists unless the signal level is at least this value). The maximum level Max is the signal level corresponding to the maximum size in respect of which LLS sizing (calculation of the PLS (polystyrene latex sphere) size based on the signal level) can be performed. The higher the peak values of the respective levels of the scattered light intensity signals 122, 124, the larger is the size that is thus calculated. However, the calculated result is the size of a PLS (hereinbelow referred to as "PLS-based size") that reflects scattered light of the same intensity as the LLS and is not the size of the LLS itself. Hereinbelow, this first type 130 will foe called "sized LLS type".

The second type 136 is the case where the signal level reaches the saturation level Max. Essentially, the second type 136 is the case in which the intensity of the reflected amounts of light 108, 116 exceeds the maximum value in respect of which sizing can be performed. Hereinbelow, the second type 136 will be referred to as the "saturated area type". Also, one or other of the following third to fifth types 138, 140, 142 is identified when a condition of a large number of successive signals, or a high density of signals, of the saturated area type 136 or of the sized LLS type 130 described above is detected.

The third type 138 represents the case where signals of the sized LLS type 130 or saturated area type 136 described above are successively detected over at least a prescribed number of tracks (for example eight tracks) in the radial direction of the semiconductor wafer 200. The successively detected signals may be exclusively of the sized LLS type 130 or exclusively of the saturated area type 136, or may include a mixture of both types 130 and 136. Successive signals belonging to the third type 138 are referred to hereinbelow as a whole as being of the "track area type".

The fourth type 140 represents the case where signals of the sized LLS type 130 or saturated area type 136 continuing over at least a prescribed distance (for example 180 μm, corresponding to eight successive laser spots 130) in the circumferential direction of the semiconductor wafer 200 (i.e. along the line of spiral scanning) are detected. The successively detected signals may foe exclusively of the sized LLS type 130 or exclusively of the saturated area type 136, or may include a mixture of both types 130 and 136. Successive signals belonging to the fourth type 140 are referred to hereinbelow as a whole as being of the "angle area type".

The fifth type 142 does not correspond with either the tracking area type 138 or angle area type 140 described above, but represents the case where a plurality of signals of the sized LLS type 130 or saturated area type 136 described above are detected at adjacent positions whose mutual separation is within a prescribed distance. The plurality of signals belonging to the fifth type 142 are referred to hereinbelow as a whole as being of the "cluster area type".

In addition, the tracking area type 138, angle area type 140 and cluster area type 142 described above are referred to hereinbelow simply by the general term "area type" 144.

Referring once more to FIG. 1, whilst scanning of the semiconductor wafer 200 is being performed by the laser spot 103 the first signal processing device 126A monitors the signal levels of the respective scattered light intensity signals 122, 124 and detects the scattered light intensity signals associated with the sized LLS type 130 and saturated area type 136, and stores the detected signal levels, type and position co-ordinates. In addition, the first signal processing device 126A, using the positional co-ordinates of the plurality of signals of the detected sized LLS type 130 and saturated area type 136, detects the scattered light intensity signals belonging to the area type 144 (tracking area type 138, angle area type 140 and cluster area type 142), and calculates the size of the region where such a signal is detected.

The second signal processing device 126B receives from the first signal processing device 126A data 125 indicating the detection result of the signals of the widely scattered light intensity signal 122 and narrowly scattered light intensity signal 124 of the sized LLS type 130, the saturated area type 136 and the area type 144 respectively described above and, by analyzing both of these detection results by the method to be described, determines the type of LLS (particle or severe defect or slight defect).

A detailed description of the analysis processing for identifying the type of LLS that is performed by the second signal processing device 126B is given below.

FIG. 3 is a view showing the most fundamental principles constituting the basis of this signal processing.

Figure 3A:
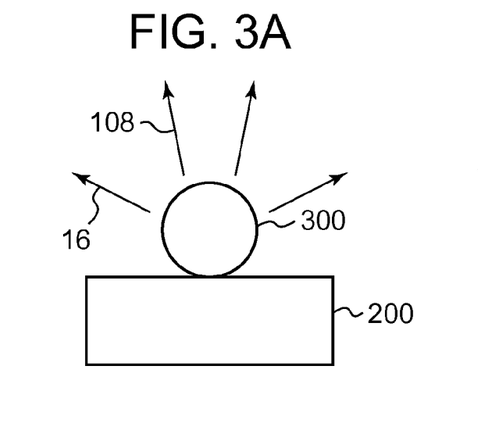
FIG. 3 is a view showing the most basic principles that are fundamental to the analysis processing for identifying types of surface abnormality, performed by the second signal processing device 126B.
Figure 3B:
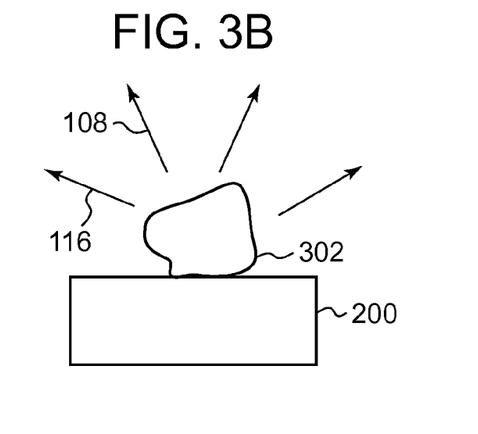
Figure 3C:
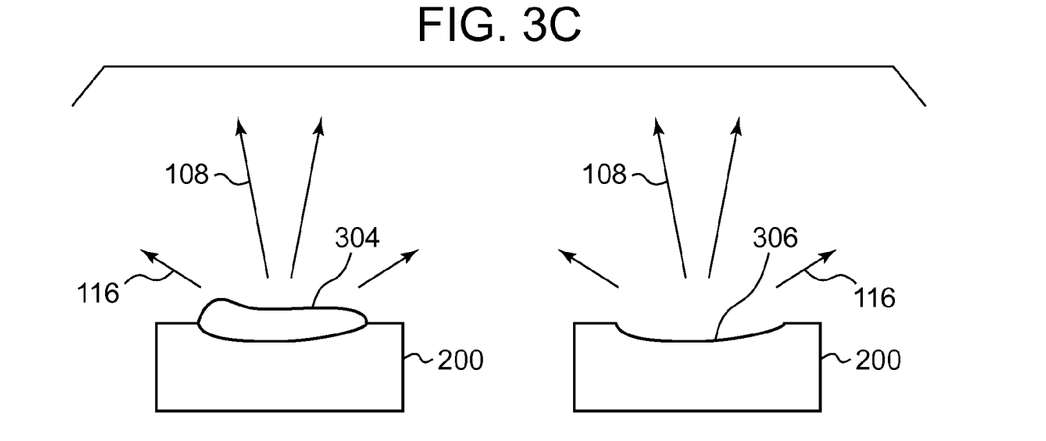
Figure 3D:
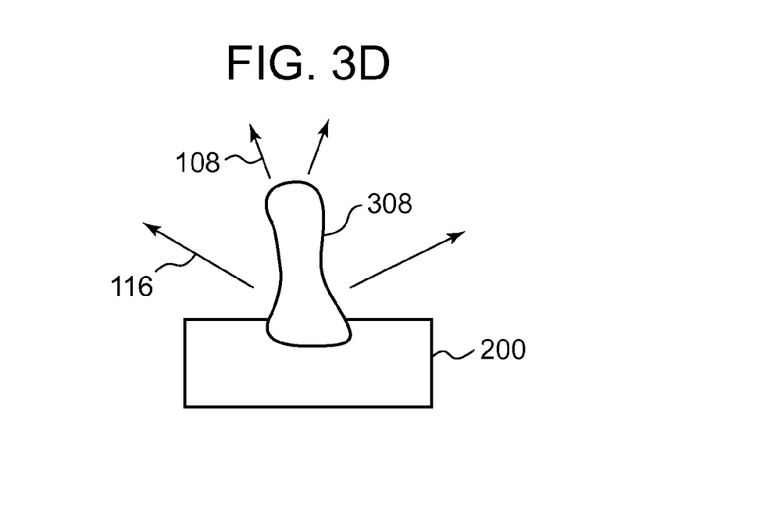

FIG. 3A shows the inferred intensity distribution of the reflected scattered light 108, 116 when a PLS 300 is located on the surface of a semiconductor wafer 200. FIG. 3B shows the inferred intensity distribution of the reflected scattered light 103, 116 when a particle 302 is located on the surface of a semiconductor wafer 200. FIG. 3C shows the inferred intensity distribution of the reflected scattered light 108, 116 when a flat protuberance 304 or shallow concavity 306 (of low height or shallow depth compared with the dimensions of the plane) exists on the surface of the semiconductor wafer 200. FIG. 3D shows the inferred intensity distribution of the reflected scattered light 108, 116 when a tower-shaped protuberance 308 (of large height compared with the dimensions of the plane) exists on the surface of the semiconductor wafer 200.

As shown in FIG. 3A, the PLS 300 is close to a perfectly spherical shape. The inspection device 100 is then calibrated so as to show the precise value of the diameter of an actual PLS 300, whether the size is calculated from the narrowly scattered light from the PLS 300 or from the widely scattered light from the PLS 300. As shown in FIG. 3B, most particles 302 may be considered as having a three-dimensional shape whose planar dimensions and height are roughly balanced, so there is not much difference between the PLS-based size of a particle 302 calculated from the narrowly scattered light 108 and the PLS-based size calculated from the widely scattered light 116; or, if the particle 302 is stabilized in a flatfish attitude, the PLS-based size calculated from, the narrowly scattered light 108 may be inferred to be somewhat larger than that calculated from the widely scattered light 116. Also, as shown in FIG. 3C, in the case of a flat protuberance 304 or concavity 306, faces that are close to horizontal will clearly foe wider than faces that are close to vertical, so the PLS-based size calculated from narrowly scattered light 108 will be inferred to be clearly larger than that calculated from widely scattered light 116. Contrariwise, as shown in FIG. 3D, in the case of a tower-shaped protuberance 308, since the faces that are close to vertical will be clearly wider than faces that are close to horizontal, the PLS-based size calculated from the widely scattered light 116 will be inferred to be clearly larger than that calculated from the narrowly scattered light 108.

Taking as an example the case of an epitaxial wafer (semiconductor having a thin epitaxial layer grown on the surface of the semiconductor based substrate), the relationship of defects thereof with the principles of FIG. 3 will be described with reference in particular to killer defects.

Most epitaxial wafer defects are stacking faults (SF) of the epitaxial layer. There are various different types of SF of the epitaxial layer, but, in most types, a flat protuberance 304 or concavity 306 as shown in FIG. 3C is formed in the surface of the epitaxial layer. Not all these SF are necessarily killer defects, but, if the size of a protuberance 304 or concavity 306 is more than a certain amount, there is a nigh likelihood that it will constitute a killer defect. For example, if a protuberance 304 or concavity 306 having a pyramidal or mesa-like geometrical three-dimensional shape with a planar dimension of the order of a few μm to a few tens of urn and a height of the order of a few tens of nm to a few hundreds of nm, or a complex three-dimensional shape comprising an irregular mixture of such shapes, is present in the surface of the epitaxial layer, this is deemed, to be a killer defect. Also, if a large number of LLS protuberances or concavities are successively aggregated over a wide region exceeding for example a total length of 100 μm in the surface of the epitaxial layer, this is termed a large area defect (LAD), which is also typically a killer defect.

Consequently, if the intensity of the narrowly scattered light 108 is markedly greater than the intensity of the widely scattered light 116, as shown in FIG. 3C, at a given detection point on the surface of the epitaxial wafer, a defect is inferred to be present at this detection point. Also, it may be assumed, that the larger the size of such a defect, the greater will be the likelihood of such a defect being a killer defect. Also, if, as shown in FIG. 3B, the intensity of the widely scattered light 116 and the intensity of the narrowly scattered light 108 at a given detection point are of the same order, or the former is slightly greater than the latter, existence of a particle at the detection point is inferred. Also, when a scattered light intensity signal of an area type 144 as shown in FIG. 2 is obtained in a given region on the surface of an epitaxial wafer, it is considered as a strong possibility that a defect of correspondingly large size or a LAD is present thereon.

In the analysis processing performed by the second signal processing device 126B, detection/identification logic is employed based on the above principles in order to identify the various types of LLS.

FIG. 4 shows an example of this detection/identification logic.

The detection/identification logic shown in FIG. 4 was obtained by the present inventors on the basis of the principles described above with reference to FIG. 3 and also as a result of repeated studies of inspections of particles or defects of various types on actual epitaxial wafers using an SP1 manufactured by KLA-Tencor Ltd.

Figures 4A, 4B:
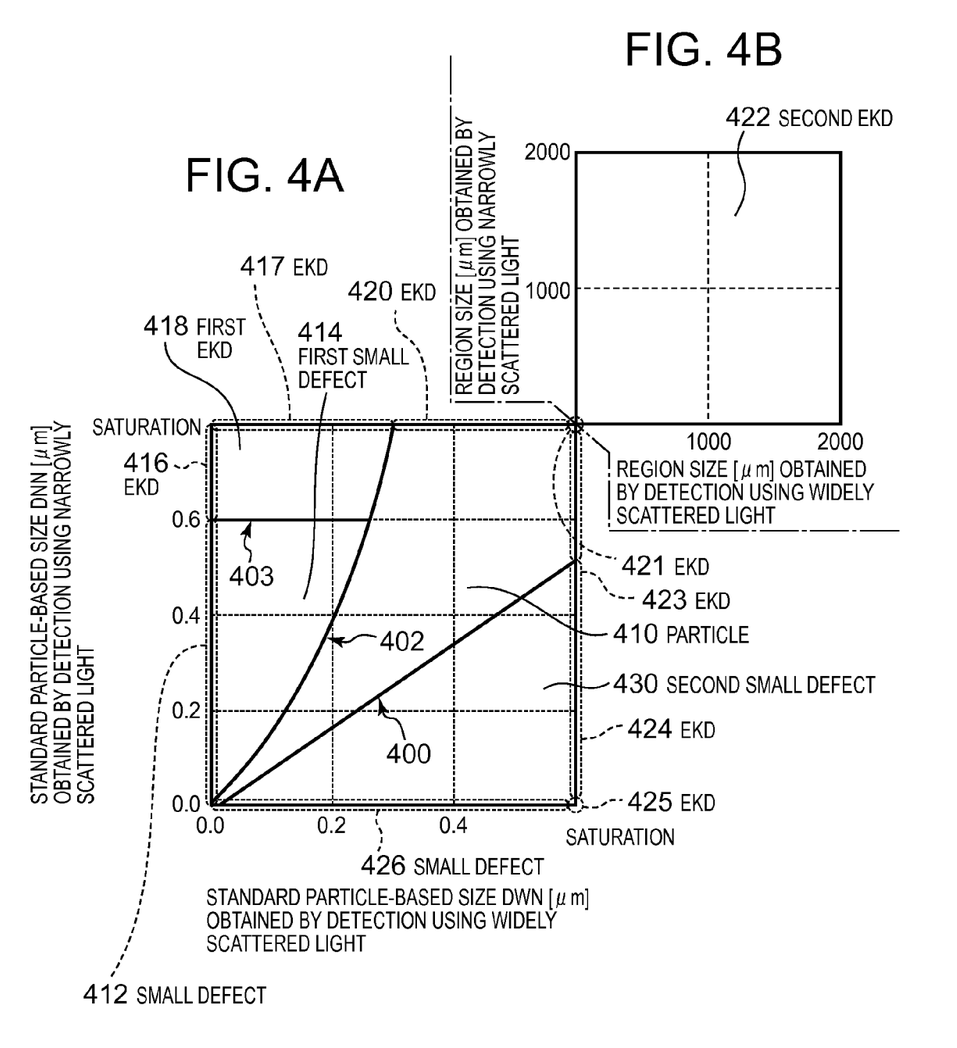
FIG. 4 is a view given in explanation of the logic for identifying types of LLS that is employed in the analysis processing performed by the second signal processing device 126B.

FIG. 4A shows the detection/identification logic applied when scattered light intensity signals 122, 124 of sized LLS type 130 and saturated, area type 136 as shown in FIG. 2 were obtained. In FIG. 4A, the horizontal axis shows the PLS-based size (diameter) DWN calculated using a widely scattered light intensity signal 124 of the sized LLS type 130; the right-hand end thereof corresponds to the case where a widely scattered light intensity signal 124 of saturated area type 136 was obtained. In FIG. 4A, the vertical axis snows the PLS-based size (diameter) DUN calculated using the narrowly scattered light intensity signal 124 of the sized LLS type 130; the upper end thereof corresponds to the case where a narrowly scattered light intensity signal 122 of the saturated area type 136 was obtained. Also, FIG. 4B shows the detection/ identification logic applied in the case where scattered light intensity signals 122, 124 of area type 144 shown in FIG. 2 were obtained. In FIG. 4B, the horizontal axis shows the size of the region where a widely scattered light intensity signal 124 of the area type 144 was detected and the horizontal axis shows the size of the region where a widely scattered light intensity signal 122 of area type 144 was detected.

In a range in which the scattered light intensity signals 124 and 122 shown in FIG. 4A are both of the sized LLD type 130 (for example range in which 0.0<DNN< about 0.8 µm, and 0.0<DWN< about 0.6 µm, hereinbelow referred to as the "sizing range"), if a signal analysis result belonging to the zone 410 is obtained from a given detection point, it is also concluded that a particle is present at that detection point. This zone is termed the "particle zone".

The particle zone 410 is a cone sandwiched between a first discrimination line 400 and a second discrimination line 402 in the sizing range and satisfies the conditions that the PLS-based size DIM obtained from widely scattered light 116 is less than about 0.6 µm and that the narrowly scattered light intensity signal 122 has not reached saturation. The first discrimination line 400 corresponds to the case where the PLS-based size OWN obtained from the widely scattered light 116 and the PLS-based size DNN obtained from the narrowly scattered light 108 are substantially of the same order (the PLS-based size DWH obtained from the widely scattered light 116 is slightly smaller than the PLS-based size DNN obtained from the narrowly scattered light 108). Hereinbelow, this first discrimination line 400 will be termed the "particle lower limit line". The particle lower limit line 400 may be expressed by for example a first order function $$DNN = K \cdot DWN$$

where K is a coefficient between 1 and 0.5, having for example a value of about 0.8 to 0.9.

The second discrimination line 402 corresponds to the case where the PLS-based size DNN obtained from the narrowly scattered light 108 is to a certain extent larger than the PLS-based size DWN obtained from the widely scattered light 116. Hereinbelow, this second discrimination line 402 will be termed the "defect separation line". The defect separation line 402 may be expressed for example by the function $$\log(DNN) = (1/S)\log(DWN) + T/S, \text{ and } DNN \geq DWN$$

Where S and T are positive coefficients of less than 1, having for example values of about 0.4 to 0.6.

The particle zone 410 essentially corresponds to the case where the PLS-based size DNN calculated from the narrowly scattered light 108 is of the same order as or is larger than the PLS-based size DWN calculated from the widely scattered light 116, within a prescribed range, under the condition that both of the narrowly scattered light intensity signal 122 and widely scattered light intensity signal 124 are of the sized LLS type. In this case, the evaluation result is obtained that a particle is present. This evaluation result conforms to the principles described with reference to FIG. 3B.

In the sizing range shown in FIG. 4A, it is concluded that a slight defect, that is inferred not to be (or unlikely to be) a killer defect, is present at the detection point where an analysis result belonging to the zone 414 was obtained (such a defect is hereinbelow termed a "small defect"). Also, at a detection point where an analysis result belonging to the zone 418 was obtained, it is concluded that a severe structural defect (hereinbelow termed "EKD (estimated killer defect)") inferred to be (or likely to be) a killer defect is present. The zone 414 is termed the "first small defect zone" and the zone 418 is termed the "first EKD cone".

The first small defect zone 414 and first EKD zone 418 are zones wherein the PLS-based size DWN obtained using the widely scattered light intensity signal 124 is smaller than the defect separation line 402. Also, the first small defect zone 414 and first EKD zone 418 are distinguished by the third discrimination line 403. The third discrimination line 403 will hereinbelow be called the "EKD separation line". The EKD separation line 403 is a line at which for example the PLS-based size DNN obtained using the narrowly scattered light intensity signal 122 corresponds to 0.6 µm. In the first small defect zone 414, the PLS-based size DNN obtained using the narrowly scattered light intensity signal 122 is less than 0.6 µm and, in the first EKD zone 418, this signal is more than 0.6 µl. In simple terms, this is a case in which the PLS-based size DNN obtained from the narrowly scattered light 108 is greater by at least a prescribed amount than the PLS-based size DWN obtained using the widely scattered light 116, in the small defect zone 414 and also the first EKD zone 418. Also, if the PLS-based size DNN detected using the narrowly scattered light 108 is less than 0.6 µm, it is concluded that a small defect is present; if the PLS-based size DUN is more than 0.6 µm, it is concluded that an EKD is present. This evaluation result is in accordance with the principles described with reference to FIG. 3C.

Also, in the sizing range indicated, in FIG. 4A, the probability that a zone 430 will actually foe detected is fairly low; it appears that this corresponds to a tower-shaped defect as shown in FIG. 3D or to a defect present in the vicinity of an edge. This zone 430 is evaluated as corresponding to a small defect as described above. Such a zone 430 is hereinbelow referred to as a "second small defect zone". The second small defect zone 430 is a zone in respect of which the PLS-based size DNN obtained using the narrowly scattered light intensity signal 122 is on the small side compared with the particle lower limit line 400.

Furthermore, FIG. 4A shows special zones 412, 416, 417, 420, 421, 423, 424, 425 and 426 at the outer edge of the first small defect 412, first EKD zone 413, particle zone 402 and second small defect zone 430 described above. The significance of these special zones 412, 416, 417, 420, 421, 423, 424, 425 and 426 is essentially that these indicate cases where at least one level of the scattered light intensity signals 122, 124 is less than the lower limiting level Min shown in FIG. 2 (i.e. no LLS detected), or that the LLS is of the saturated area type 136. The special zone 412 adjacent to the first small defect zone is evaluated as corresponding to a small defect. The two special zones 416 and 417 adjacent to the first EKD zone 418 are both evaluated as EKD. The three special zones 420, 421 and 423 adjacent to the particle zone 410 are evaluated as EKD. The two special zone levels 424 and 425 corresponding to the saturated area type 136 adjacent to the second small defect zone 430 are also evaluated as EKD. The special zone 426 corresponding to DNN-0.0 µm adjacent to the second defect zone 430 is evaluated as a small defect.

Figure 5:
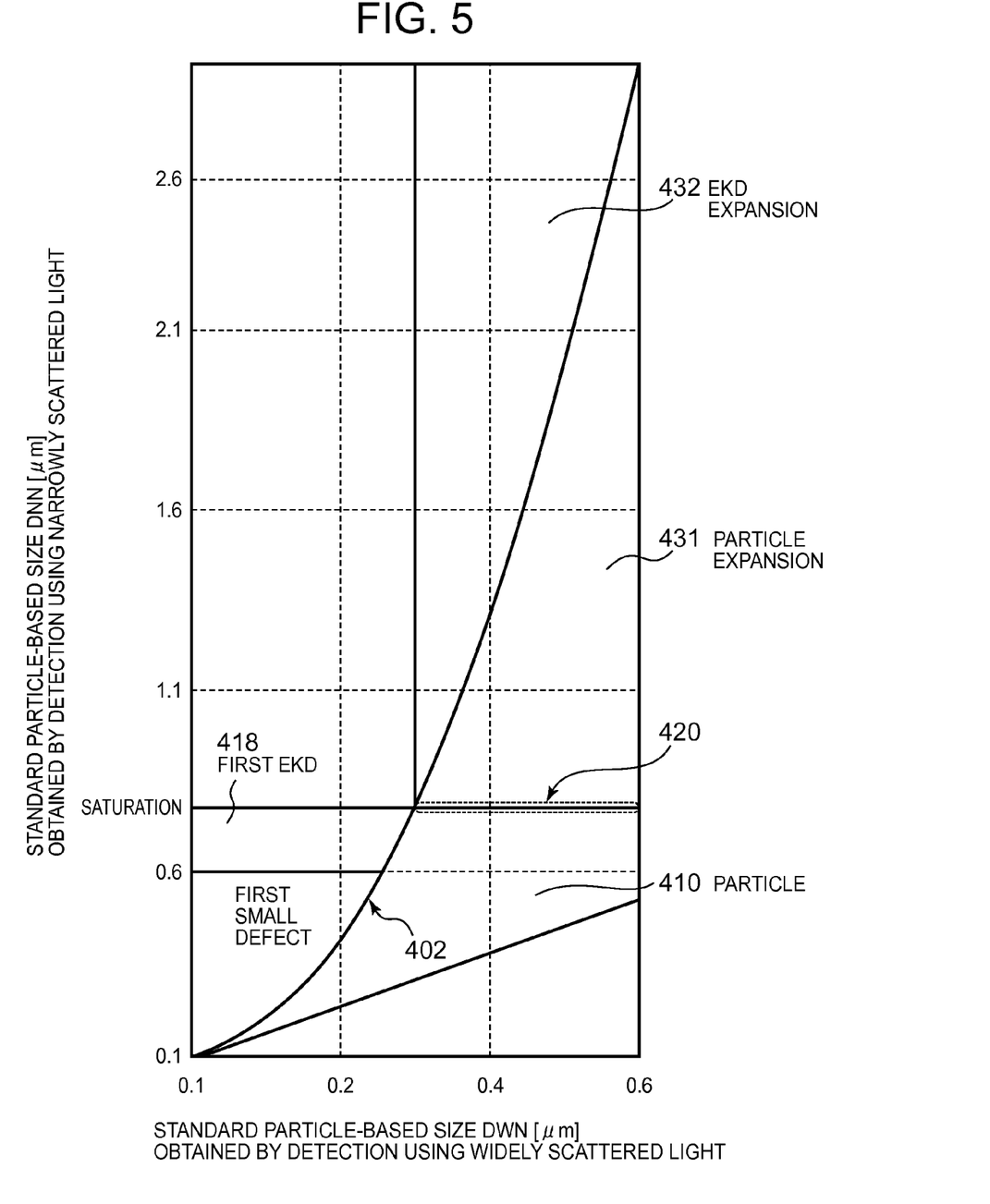
FIG. 5 is a view given in explanation of the theoretical significance of the second EKD zone 420.

However, in the case of the special zone 420 adjacent to the particle zone 410, the narrowly scattered light intensity signal 122 is of the saturated area type, whereas the widely scattered light intensity signal 124 is of the sized LLS type; this is a case in which the PLS-based size DWN that is thereby obtained is at least 0.3 µm. As shown theoretically in FIG. 5, this special zone 420 appears to be a projection region of the particle expansion region 431 on the extension of the particle zone 410 and is also a projection region of the EKD expansion region 432 on the extension of the first EKD zone 418. Consequently, a particle or EKD may also theoretically foe present in the special zone 420. However, in practice, this problem can be avoided by choice of a suitable value of the saturation size of the DNN. According to the studies made by the present inventors, by setting the DNN saturation value to about 0.8 μm, it was found that substantially all of the laser light scatterers on the special zone 420 were EKDs. It is therefore concluded that an EKD is present in this special zone 420.

The zone 422 shown in FIG. 4B represents the case where both the narrowly scattered optical signal 122 and scattered light intensity signal 124 are of the saturated area type 136 or area type 144 shown in FIG. 2. The minimum values of the vertical axis and horizontal axis of this zone 422 are values that are larger than the maximum values of the PLS-based size DNN and DWN that may be calculated using sized LLS type 130 signals, it may be concluded that an EKD as described above is present at the detection point where an analysis result belonging to this zone 422 was obtained. This zone 422 is called the "second EKD zone".

Figure 6:
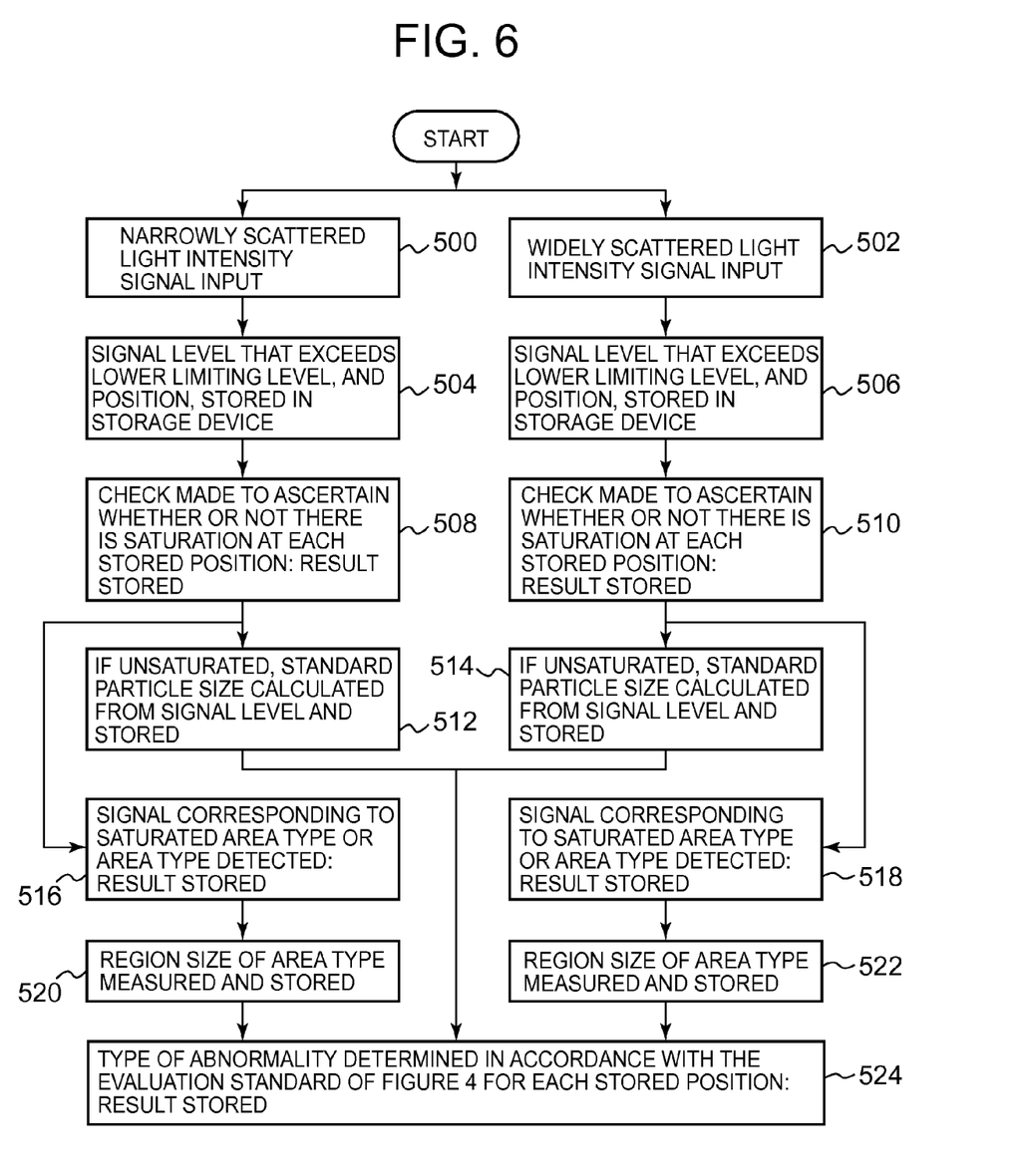
FIG. 6 is a view showing the flow of analysis processing carried out by the signal processing devices 126A and 126B.

FIG. 6 shows the flow of analysis processing performed using the signal processing devices 126A and 126B in surface inspection of a semiconductor wafer.

As described with reference to FIG. 1, the steps 500, 502, 504 and 506 shown in FIG. 6 are continuously executed during scanning of the surface of a semiconductor wafer 200 with a light spot 103. In the steps 500 and 502, the narrowly scattered light intensity signal 122 and widely scattered light intensity signal 124 from the current detection point are input simultaneously to the first signal processing device 126A. In steps 504 and 506, if the respective signal levels of the narrowly scattered light intensity signal 122 and widely scattered light intensity signal 124 exceed the lower limiting level Min shown in FIG. 2, these signal levels and the positional-co-ordinates of the point of detection are stored in a storage device (not shown) within the first signal processing device 126A.

The routine subsequent to steps 508 and 510 may be performed whilst the above scanning is being performed, or may be performed after the above scanning has been terminated.

In step 508, a check is made to ascertain whether the signal, level of the narrowly scattered light intensity signal 122 detected at this position has reached the saturated level Max, or is less than this (i.e. is unsaturated), at each of the positional co-ordinates of the detection points stored in the storage device in the first signal processing device 126A. In step 510, a check is made to ascertain whether the signal level of the widely scattered light intensity signal 124 detected at this position has reached the saturation level Max, or is less than this (i.e. is unsaturated), at each of the positional co-ordinates of the detection points stored in the storage device in the signal processing device 126.

In step 512, if the result of the check of step 508 is "unsaturated" (i.e. that the narrowly scattered light intensity signal 122 is of the sized LLS type 130), the PLS-based size DNN is calculated based on the signal level of this narrowly scattered light intensity signal 122, and the PLS-based size DNN is stored in the storage device in association with the positional co-ordinates of the corresponding detection point. In step 514, if the result of the check of step 510 is "unsaturated" (i.e. that the widely scattered light intensity signal 124 is of the sized LLS type 130), the PLS-based size DWN is calculated based on the signal level of this widely scattered light intensity signal 124, and the PLS-based size DWN is stored in the storage device in association with the positional co-ordinates of the corresponding detection point.

In step 516, a check is made to ascertain whether a narrowly scattered light intensity signal 122 is present corresponding to the saturated area type 136 and area type 144 and the result of this check is stored in the storage device in association with the positional co-ordinates of the corresponding point of detection. In step 518, a check is made to ascertain whether a widely scattered light intensity signal 124 is present corresponding to the saturated area type 136 and area type 144 and the result of this check is stored in the storage device in association with the positional co-ordinates of the corresponding point of detection.

In step 520, if the result of the check performed in step 516 indicates area type 144, the size of the region where a narrowly scattered light intensity signal 122 of this area type 144 was detected is calculated using the positional co-ordinates of the plurality of corresponding detection points and the size of this region is stored in the storage device in association with the positional co-ordinates of the corresponding detection points. In step 522, if the check result of step 518 indicates area type 144, the size of the region where the widely scattered light intensity signal 124 of this area type 144 was detected is calculated, using the positional co-ordinates of the plurality of corresponding detection points, and the size of this region is then stored in the storage device in association with the positional co-ordinates of the corresponding detection points.

In step 524, data indicating the positional co-ordinates of the detection points stored in the storage device, the PLS-based size DNN or region size obtained using the narrowly scattered light intensity signal 122, and the PLS-based size DWN or region size obtained using the widely scattered light intensity signal 124 are transferred to the second signal processing device 126B. The second signal processing device 126B uses this data to evaluate, in accordance with the detection/evaluation logic already described and shown in FIG. 4, at which positions on the semiconductor wafer 200 an LLS is present or not, and, if an LLS is present, whether this LLS is a particle, small defect or EKD. This evaluation result is stored in the storage device in association with the positional co-ordinates of the corresponding detection point and whether or not the semiconductor wafer 200 is satisfactory is decided in accordance therewith. The results of these evaluations or decisions are output to the outside for display of the detection results or in order for further analysis to be performed, and the wafer manipulator 129 separates the semiconductor wafers 200 in accordance with the results of this decision regarding suitability.

With the inspection device 100 and inspection method described above with reference to the drawings, inspection can be performed even though no selective etching of the surface of the semiconductor wafer 200, such as was performed prior to inspection in the conventional inspection method, has been carried out. This inspection device 100 and inspection method are therefore suitable for application to mass-production.

While embodiments of the present invention have been described above, these embodiments are merely given by way of example for explanation of the present invention and the scope of the present invention is not intended to be restricted solely to these embodiments. The present invention can be put into practice in various other modes, without departing from its essence.

The invention claimed is:

1. A semiconductor wafer inspection device comprising:
an optical illumination device that directs a light spot onto an inspection point on a surface of the semiconductor wafer;
a first optical sensor that, of scattered light from said inspection point, receives narrowly scattered light scattered with a scattering angle that is narrower than a prescribed angle and detects intensity of said narrowly scattered light;

a second optical sensor that, of scattered light from said inspection point, receives widely scattered light scattered with a scattering angle that is wider than a prescribed angle and detects intensity of said widely scattered light; and a signal processing circuit that identifies the type of laser light scatterer present at said inspection point in response to a detection signal from said first and second optical sensors, wherein said signal processing circuit comprises:

first calculation means that, if the intensity of said narrowly scattered light is within a prescribed sizing range, calculates a first PLS-based size from the intensity of said narrowly scattered, light;

second calculation means that, if the intensity of said widely scattered light is within said sizing range, calculates a second PLS-based size from the intensity of said widely scattered light; and identification means that, if the intensities of said narrowly scattered light and said widely scattered light are both within said sizing range, identifies the type of said laser light scatterer in accordance with both the first PLS-based size and said second. PLS-based size.

2. The semiconductor wafer inspection device according to claim 1, wherein said identification means identifies a laser light scatterer present at said inspection point as being a particle, in a prescribed particle zone in which said first PLS-based size in said sizing range is either substantially equal to said second PLS-based size or is larger than said second PLS-based size, by a degree not more than a prescribed degree.

3. The semiconductor wafer inspection device according to claim 1, wherein said identification means identifies a laser light scatterer present at said inspection point as being a defect, in a prescribed defect zone in which said first PLS-based size in said sizing range is larger than said second PLS-based size, by a degree not less than said prescribed degree.

4. The semiconductor wafer inspection device according to claim 3, wherein said identification means identifies whether said defect is assumed to be a killer defect or not, in accordance with whether the first PLS-based size is larger or smaller than a prescribed size, in said prescribed defect zone.

5. The semiconductor wafer inspection device according to claim 1, wherein said identification means identifies a laser light scatterer present at said inspection point as being a defect that is assumed to be a killer defect if the intensity of said narrowly scattered light or said widely scattered light exceeds said sizing range.

6. A method of inspection of semiconductor wafers comprising:

a step of directing a light spot onto an inspection point on a surface of the semiconductor wafer;

a step of detecting intensity, of scattered light from said inspection point, of narrowly scattered light scattered with a scattering angle that is narrower than a prescribed angle;

a step of detecting intensity, of scattered light from said inspection point, of widely scattered light scattered with a scattering angle that is wider than a prescribed angle;

a step of, if the intensity of said narrowly scattered light is within a prescribed sizing range, calculating a first PLS-based size from the intensity of said narrowly scattered light;

a step of, if the intensity of said widely scattered light is within said sizing range, calculating a second PLS-based size from the intensity of said widely scattered light; and a step of, if the intensities of said narrowly scattered light and said widely scattered light are both within said sizing range, identifying the type of laser light scatterer present at said inspection point in accordance with both said first PLS-based size and said second PLS-based size.

* * * * *